(12) United States Patent
Ra et al.

(10) Patent No.: US 9,982,234 B2
(45) Date of Patent: May 29, 2018

(54) CULTURE MEDIUM COMPOSITION FOR IMPROVING REGENERATIVE CAPACITY OF STEM CELLS, AND STEM CELL CULTURING METHOD USING SAME

(71) Applicants: R BIO CO., LTD., Seoul (KR); Jeong-Chan Ra, Suwon-si Gyeonggi-do (KR)

(72) Inventors: Jeong-Chan Ra, Suwon-si (KR); Sung Keun Kang, Seoul (KR); Jung Youn Jo, Seoul (KR)

(73) Assignees: R BIO CO., LTD, Seoul (KR); Jeong-Chan Ra, Gyeonggi-Do (KR)

( * ) Notice: Subject to any disclaimer, the term of this patent is extended or adjusted under 35 U.S.C. 154(b) by 0 days. days.

(21) Appl. No.: 14/889,434

(22) PCT Filed: Feb. 6, 2014

(86) PCT No.: PCT/KR2014/001013
§ 371 (c)(1),
(2) Date: Nov. 5, 2015

(87) PCT Pub. No.: WO2014/181954
PCT Pub. Date: Nov. 13, 2014

(65) Prior Publication Data
US 2016/0090573 A1 Mar. 31, 2016

(30) Foreign Application Priority Data
May 9, 2013 (KR) ........................ 10-2013-0052558

(51) Int. Cl.
*C12N 5/0775* (2010.01)
(52) U.S. Cl.
CPC ........ *C12N 5/0667* (2013.01); *C12N 2500/14* (2013.01); *C12N 2500/25* (2013.01); *C12N 2500/30* (2013.01); *C12N 2500/32* (2013.01); *C12N 2500/38* (2013.01); *C12N 2500/76* (2013.01); *C12N 2501/11* (2013.01); *C12N 2501/115* (2013.01); *C12N 2501/33* (2013.01); *C12N 2501/39* (2013.01); *C12N 2501/40* (2013.01); *C12N 2501/998* (2013.01); *C12N 2501/999* (2013.01)

(58) Field of Classification Search
CPC combination set(s) only.
See application file for complete search history.

(56) References Cited

U.S. PATENT DOCUMENTS

2006/0177418 A1 8/2006 Braiman-Wiksman et al.
2011/0269230 A1* 11/2011 Marban ................ C12N 5/0657
435/375

FOREIGN PATENT DOCUMENTS

| CN | 101735980 A | 6/2010 |
|---|---|---|
| CN | 103060264 A | 4/2013 |
| KR | 100795708 B1 | 1/2008 |
| KR | 100818214 B1 | 4/2008 |
| WO | 03046141 A2 | 6/2003 |
| WO | 2006019357 A1 | 2/2006 |
| WO | 2007145438 A1 | 12/2007 |
| WO | 2010008219 A2 | 1/2010 |
| WO | 2010057614 A1 | 5/2010 |
| WO | 2012074265 A2 | 6/2012 |

OTHER PUBLICATIONS

Attane et al, "Apelin stimulates glucose uptake but not lipolysis in human adipose tissue ex vivo" Journal of Molecular Endocrinology, 2011, vol. 46, pp. 21-28.*
Than et al, "Apelin inhibits adipogenesis and lipolysis through distinct molecular pathways" Molecular and Cellular Endocrinology, 2012, vol. 362, pp. 227-241.*
Bonab, M., et al., "Aging of mesenchymal stem cell in vitro", "BMC Cell Biology", Mar. 10, 2006, pp. 1-7, vol. 7, No. 14.
Devic, E., et al., "Expression of a new G protein-coupled receptor X-msr is associated with an endothelial lineage in Xenopus laevis", "Mechanisms of Development", Oct. 1996, pp. 129-140, vol. 59
Kleinz, M., et al., "Emerging roles of apelin in biology and medicine", "Pharmacology & Therapeutics", Aug. 2005, pp. 198-211, vol. 107.
Lee, D., et al., "Characterization of apelin, the ligand for the APJ receptor", "Journal of Neurochemistry", Jan. 2000, pp. 34-41, vol. 74.
Mesmin, C., et al., "Liquid chromatography/tandem mass spectrometry assay for the absolute quantification of the expected circulating apelin peptides in human plasma", "Rapid Communications in Mass Spectrometry", Oct. 15, 2010, pp. 2875-2884, vol. 24.
Mottaghi, S., et al., "Apelin 13: a novel approach to enhance efficacy of hypoxic preconditioned mesenchymal stem cells for cell therapy of diabetes", "Medical Hypotheses", Sep. 11, 2012, pp. 717-718, vol. 79.
O'Dowd, B., et al., "A human gene that shows identity with the gene encoding the angiotensin receptor is located on chromosome 11", "Gene", Dec. 22, 1993, pp. 355-360, vol. 136.
Szokodi, I., et al., "Apelin, the novel endogenous ligand of the orphan receptor APJ, regulates cardiac contractility", "Circulation Research", Sep. 6, 2002, pp. 435-440, vol. 91.
Tatemoto, K., et al., "Isolation and characterization of a novel endogenous peptide ligand for the human APJ receptor", "Biochemical and Biophysical Research Communications", Oct. 20, 1998, pp. 471-476, vol. 251.
Wang, I., et al., "Apelin enhances directed cardiac differentiation of mouse and human embryonic stem cells", "PLoS ONE", Jun. 1, 2012, p. e38328 (1-9), vol. 7, No. 6.

(Continued)

*Primary Examiner* — Allison M Fox
(74) *Attorney, Agent, or Firm* — Hultquist, PLLC; Steven J. Hultquist (57) ABSTRACT

The present invention relates to a medium composition for enhancing the self-renewal ability of stem cells, which contains apelin, and a method of culturing stem cells using the medium composition. According to the present invention, stem cells can be effectively cultured to proliferate without changing the characteristics of the cells, and the telomerase activity of stem cells can be increased. Thus, the efficacy of cell therapy based on stem cells can be significantly improved.

5 Claims, 4 Drawing Sheets

(56) References Cited

OTHER PUBLICATIONS

Zeng, X., et al., "Protective effect of apelin on cultured rat bone marrow mesenchymal stem cells against apoptosis", "Stem Cell Research", Dec. 13, 2011, pp. 357-367, vol. 8, No. 3.

Blagosklonny, M., "Aging, Stem Cells, and Mammalian Target of Rapamycin: A Prospect of Pharmacologic Rejuvenation of Aging Stem Cells", "Rejuvenation Research", Jun. 5, 2008, pp. 801-808, vol. 11, No. 4.

Conboy, I., et al, "Rejuvination of Aged Progenitor Cells by Exposure to a Young Systemic Environment", "Nature", Feb. 17, 2005, pp. 760-764, vol. 433, No. 7927.

Lund, T., et al., "Mesenchymal Stem Cells from Donors Varying Widely in Age are of Equal Cellular Fitness After in vitro Expansion Under Hypoxic Conditions", "Cytotherapy", Jul. 6, 2010, pp. 971-981, vol. 12, No. 8.

Madonna, R., et al, "Enhanced Survival and Myocardin-A Induced Cariomyogenesis in Aged Mesenchymal Stem ells Rejuvenated by Human Telomerase Gene Transfer", "Late-Breaking Basic Science Abstracts from the American Heart Association's Scientific Sessions 2011", "Circulation Research", Nov. 11, 2011, pp. e57-e58, vol. 109, No. 12, Abstract No. 26401.

Madonna, R., et al, "Mesenchymal Stem Cells Rejuvenation Afforded by Human Telomerase Gene Transfer Restored Myogenic Responses and Suppressed Fas-Mediated Apoptosis via Induction of Myocardin-A", "Cardiovascular Research Supplements", 2012, p. 40, vol. 93, No. 1.

Neupane, M., et al, "Isolation and Characterization of Canine Adipose-Derived Mesenchymal Stem Cells", "Tissue Engineering: Part A", 2008, pp. 1007-1015, vol. 14, No. 6.

Sun, Y., et al, "Rescuing Replication and Osteogenesis of Aged Mesenchymal Stem Cells by Exposure to a Young Extracellular Matrix", "The FASEB Journal", Jan. 6, 2011, pp. 1474-1485, vol. 25, No. 5.

Zheng, W., et al., "Loss of Proliferation and Differentiation Capacity of Aged Human Periodontal Ligament Stem Cells and Rejuvenation by Exposure to the Young Extrinsic Environment", "Tissue Engineering: Part A", Feb. 20, 2009, pp. 2263-2371, vol. 15, No. 9.

Helledie, T., et al., "Heparan Sulfate Enhances the Self-Renewal and Therapeutic Potential of Mesenchymal Stem Cells from Human Adult Bone Marrow", "Stem Cells and Development", Nov. 9, 2011, pp. 1897-1910, vol. 21, No. 11.

Li, L, et al., "Effects of Apelin-13 on Rat Bone Marrow-Derived Mesenchymal Stem Cell Proliferation Through the AKT/GSK3b/Cyclin D1 Pathway", "International Journal of Peptide Research and Therapeutics", Apr. 5, 2014, pp. 421-425, vol. 20.

Tang, S-Y., et al., "Apelin stimulates proliferation and suppresses apoptosis of mouse osteoblastic cell line MC3T3-E1 via JNK and PI3-K/Akt signaling pathways", "Peptides", Nov. 5, 2006, pp. 708-718, vol. 28.

Deeb, D., et al., "Inhibition of cell proliferation and induction of apoptosis by oleanane triterpenoid (CDDO-Me) in pancreatic cancer cells is associated with the suppression of hTERT gene expression and its telomerase activity", "Biochemical and Biophysical Research Communication", May 16, 2012, pp. 561-567, vol. 422.

Ge, J., et al., "Effects of telomerase activity and apoptosis on ex vivo expansion of cord blood CD34 cells", "Cell Proliferation", Feb. 2013, pp. 38-44, vol. 46.

Holt, S. E., et al., "Resistance to Apoptosis in Human Cells Conferred by Telomerase Function and Telomere Stability", "Molecular Carcinogenesis", Aug. 1999, pp. 241-248, vol. 25.

Mormile, R., et al., "Is telomerase the final downstream effector of the escape of cardiomyocytes from the point-of-no-return of apoptosis in infants of diabetic mothers?", "International Journal of Cardiology", Jul. 20, 2011, pp. 378-379, vol. 151.

\* cited by examiner

CULTURE MEDIUM COMPOSITION FOR IMPROVING REGENERATIVE CAPACITY OF STEM CELLS, AND STEM CELL CULTURING METHOD USING SAME

TECHNICAL FIELD

The present invention relates to a medium composition for enhancing self-renewal ability of stem cells, and a method of culturing stem cells using the same, and more particularly, to a medium composition for culturing stem cells, which can enhance the self-renewal ability of stem cells without changing the size and activity of the stem cells, so that the self-renewal ability of stem cells of old people will be enhanced to a level comparable to that of stem cells of young people, and a method of culturing stem cells using the medium composition.

BACKGROUND ART

Stem cells refer to cells having not only self-replicating ability but also the ability to differentiate into at least two types of cells, and can be divided into totipotent stem cells, pluripotent stem cells, and multipotent stem cells. Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside of blastocysts generated 4-5 days after fertilization. These cells are called "embryonic stem cells" and can differentiate into various other tissue cells but not form new living organisms. Multipotent stem cells, which are stem cells capable of differentiating into only cells specific to tissues and organs containing these cells, are involved not only in the growth and development of various tissues and organs in the fetal, neonatal and adult periods but also in the maintenance of homeostasis of adult tissue and the function of inducing regeneration upon tissue damage. Tissue-specific multipotent cells are collectively called "adult stem cells".

Adult stem cells are obtained by taking cells from various human organs and developing the cells into stem cells and are characterized in that they differentiate into only specific tissues. However, recently, experiments for differentiating adult stem cells into various tissues, including liver cells, were dramatically successful, which comes into spotlight. In particular, efforts have been made in the field of regenerative medicine for regenerating biological tissues and organs and recovering their functions that were lost due to illness or accident and the like by using cells. Methods which are frequently used in this field of regenerative medicine comprise the steps of: collecting stem cells, blood-derived mononuclear cells or marrow-derived mononuclear cells from a patient; inducing the proliferation and/or differentiation of the cells by tube culture; and introducing the selected undifferentiated (stem cells and/or progenitor cells) and/or differentiated cells into the patient's body by transplantation. Accordingly, existing classical methods for treating diseases by medication or surgery are expected to be replaced with cell/tissue replacement therapy which replaces a damage cell, tissue or organ with healthy one, and thus the utility of stem cells will further increase.

Thus, the various functions of stem cells are currently being studied. Particularly, since cell therapy technologies using mesenchymal stem cells started to receive attention, technologies for improving mesenchymal stem cells isolated from a human body so as to be suitable for therapeutic purposes have been developed (WO 2006/019357, Korean Patent No. 0795708, and Korean Patent No. 0818214).

Meanwhile, the function of the body's organs or the ability of cells to self-renew decreases with age. Similar to this phenomenon, the function and morphology of stem cells can change when the stem cells are repeatedly cultured in vitro or are stimulated by external factors. In other words, the moment the culture of cells in vitro is started, the cells start to lose their function and enter a senescence state, even though the loss of the function is almost not perceivable. Because such characteristics of cells, it is preferable to use early-stage cells for gene therapy, and it is also preferable to use stem cells that do not significantly change their characteristics, such as proliferation ability, differentiation ability, phenotype, morphology and activity, even when the stem cells are cultured for a long period of time. Thus, studies on such cells are in progress (*BMC Cell Biology* 2006, 7:14, *Aging Research Reviews* 5, 2006, 91116).

Accordingly, the present inventors have made extensive efforts to find medium components which can enhance the self-renewal ability of stem cells without changing the characteristics (such as morphology or activity) of the stem cells even when the stem cells are repeatedly cultured. As a result, the present inventors have found that, when stem cells are cultured in a medium composition containing apelin, the ability of the stem cells to self-renew can be enhanced, thereby completing the present invention.

DISCLOSURE OF INVENTION

It is an object of the present invention to provide a medium composition for enhancing the self-renewal ability of stem cells, which can enhance the self-renewal ability of stem cells of old people to a level comparable to that of stem cells of young people, and a method of culturing stem cells using the medium composition.

To achieve the above object, the present invention provides a medium composition for culturing stem cells, which contain apelin.

The present invention also provides a method for enhancing the self-renewal ability of stem cells, the method comprising a step of culturing stem cells in a medium composition containing apelin.

Other features and embodiments of the present invention will be more apparent from the following detailed descriptions and the appended claims.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein are well known and are commonly employed in the art.

As used herein, the term "stem cells" refer to cells having not only self-replicating ability but also the ability to differentiate into at least two types of cells. "Adult stem cells" refer to stem cells that appear either in the stage in which each organ of an embryo is formed after the developmental process or in the adult stage.

As used herein, the term "mesenchymal stem cells" refers to undifferentiated stem cells that are isolated from human or mammalian tissue and may be derived from various tissues. Particularly, the mesenchymal stem cells may be umbilical cord-derived mesenchymal stem cells, umbilical cord blood-derived mesenchymal stem cells, bone marrow-derived mesenchymal stem cells, adipose-derived mesenchymal stem cells, muscle-derived mesenchymal stem cells, nerve-derived mesenchymal stem cells, skin-derived mesenchymal stem cells, amnion-derived mesenchymal stem cells, or placenta-derived mesenchymal stem cells. Technology for isolating stem cells from each tissue is already known in the art.

As used herein, "adipose tissue-derived mesenchymal stem cells" are undifferentiated adult stem cells isolated from adipose tissue and are also referred to herein as "adipose-derived adult stem cells", "adipose stem cells", or "adipose-derived stem cells". These cells can be obtained according to any conventional method known in the art. A method for isolating adipose tissue-derived mesenchymal stem cells may be, for example, as follows. That is, adipose-derived mesenchymal stem cells can be isolated by culturing an adipose-containing suspension (in physiological saline) obtained by liposuction, and then either collecting a stem cell layer, attached to a culture container such as a flask, by trypsin treatment, or directly collecting those suspended in a small amount of physiological saline by rubbing with a scraper.

As used herein, the expression "without changing the size of stem cells" means that the morphology or size of stem cells is maintained similar to that before the stem cells are cultured in a medium composition.

As used herein, the term "medium" or "culture medium" means a medium capable of supporting the growth and survival of stem cells under in vitro culture conditions, and is intended to include all conventional media known in the art to be suitable for the culture of stem cells. In addition, a medium and culture conditions, which are used in the present invention, may be selected depending on the type of cells to be cultured.

As used herein, the term "proliferation" means an increase in the number of cells and has the same meaning as growth.

As used herein, the expression "self-renewal ability" or "ability of cells to self-renew" means the capability of cells to renew themselves. When the ability of cells to self-renew is enhanced, the ability of the cells to proliferate is also enhanced.

As used herein, the term "subculture" means that a portion of cells is periodically passaged by transferring them to a new culture vessel and by replacing the culture medium with a fresh culture for the long-term culture of healthy cells. As the number of cells increases in the limited space of the culture vessel, the cells die naturally due to nutrient depletion or waste accumulation in a predetermined time. Thus, subculture is used to increase the number of healthy cells. Typically, 1 passage means culture by one replacement of medium (culture vessel) or one isolation of cell population. Any subculture method known in the art may be used without any limitation, but a mechanical or enzymatic isolation method may be preferably performed.

Stem cells have problems in that, when the cells are repeatedly cultured or receive external stimuli, the morphology or size of the cells is minutely changed and the self-renewal ability and telomerase activity of the cells are reduced, that is, the cells enter senescence. Because the self-renewal ability and telomerase activity of cells differ between media in which the cells are cultured, it is important to culture stem cells in a medium composition which does not reduce the self-renewal ability or telomerase activity of the cells without significantly changing the characteristics of the cells even when the cells are repeatedly cultured. In other words, it is important to culture stem cells in a medium composition which delays or alleviates the senescence of the cells or maintains the cells in the initial state.

However, in the case in which stem cells are cultured in conventional medium compositions, the stem cells should be subcultured several times in order to increase the yield of the stem cells, and thus large amounts of manpower and time are required. Particularly, in this case, some of the medium components required for subculture are very costly, and thus the conventional medium compositions are disadvantageous in economic terms. In addition, there is a problem in that the self-renewal ability of the cells is reduced due to repeated subculture. To overcome these problems, the present invention provides a medium composition capable of enhancing the self-renewal ability of cells without changing the morphology or activity of the cells.

Thus, in one aspect, the present invention is directed to a medium composition for culturing stem cells, which contain apelin.

"Apelin" that is used in the present invention was found in rat and bovine milk in 1988 b Professor Fujino M team. It is a new peptide abundant in colostrum and is a protein that is encoded by APLN gene in humans (Tatemoto K et al., (1998). "Isolation and characterization of a novel endogenous peptide ligand for the human APJ receptor". *Biochem. Biophys. Res. Commun.* 251 (2): 4716. doi:10.1006/bbrc.1998.9489. PMID9792798). Also, it is an endogenous ligand for the G-protein-coupled APJ receptor that is expressed at the surface of some cell types (Lee D K et al., (2000). "Characterization of apelin, the ligand for the APJ receptor", *J. Neurochem.* 74 (1): 3441. doi:10.1046/j.1471-4159.2000.0740034.x. PMID10617103. Szokodi I et al., (2002). "Apelin, the novel endogenous ligand of the orphan receptor APJ, regulates cardiac contractility". *Circ. Res.* 91 (5): 43440. doi:10.1161/01.RES.0000033522.37861.69. PMID12215493, Kleinz M J, Davenport A P (2005).

"Emerging roles of apelin in biology and medicine". *Pharmacol. Ther.* 107 (2): 198211. doi:10.1016/j.pharmthera.2005.04.001. PMID15907343, O'Dowd B F et al., (December 1993). "A human gene that shows identity with the gene encoding the angiotensin receptor is located on chromosome 11". *Gene* 136 (12): 35560. doi:10.1016/0378-1119(93)90495-O. PMID8294032, Devic E et al., (October 1996). "Expression of a new G protein-coupled receptor X-msr is associated with an endothelial lineage in *Xenopus laevis*". Mech. Dev. 59 (2): 12940. doi:10.1016/0925-4773 (96)00585-0. PMID8951791). Apelin is widely expressed in the heart, liver, lung, kidney, adipose tissue, gastrointestinal tract, brain, adrenal glands, endothelium, and human plasma over various periods of time. Among them, vascular endothelial tissue shows high expression of apelin.

The apelin gene encodes a pre-proprotein of 77 amino acids, with a signal protein in the N-terminal region. Several active fragments (apelin-36, apelin-19, apelin-17, apelin-16, apelin-13 and apelin-12) share relatively similar biological activities (Invited Review Article, Targeting the ACE2 and Apelin Pathways are Novel Therapies for Heart Failure: Opportunities and Challenges. More specifically, after translocation into the endoplasmic reticulum and cleavage of the signal protein, the proprotein of 55 amino acids resulting from can generate several active fragments: a 36-amino acid peptide corresponding to the sequence 42-77 (apelin 36); a 17-amino acid peptide corresponding to the sequence 61-77 (apelin 17); and a 13-amino acid peptide corresponding to the sequence 65-77 (apelin 13). This latter fragment may also undergo a pyroglutamylation (that is a process of forming an ester of pyroglutamic acid in N-terminal glutamine) at the level of its N-terminal glutamine residue. However, the concentrations of these peptides in human plasma are not yet well known (Mesmin C, Dubois M, Becher F, Fenaille F, Ezan E (2010). "Liquid chromatography/tandem mass spectrometry assay for the absolute quantification of the expected circulating apelin peptides in human plasma". *Rapid Commun Mass Spectrom* 24 (19): 287584. doi:10.1002/rcm.4718. PMID20857448). Regarding apelin, a membrane receptor that is a family of G protein-coupled receptors or a signal pathway that interacts with several potential ligands was found by Audigier in 2006. The sites of receptor expression are linked to the different functions played by apelin in the organism (excerpt from Wikipedia). The activity of the apelin receptor initiates a change in cell activity by binding to an apelin peptide. It is known that apelin can be used as a biomarker of heart failure and is involved directly in biological effects, including vasoconstriction and vasodilation. Recent studies reported that apelin and the apelin receptor system are associated with vasculogenesis and are closely associated with diseases of the vascular system. The functions of apelin and its receptor are important in human physiology and pathological physiology. For example, it is known that apelin produces nitric oxide in vasodilation to activate L-arginine/nitric oxide synthase (NOS) and is also associated with the roles of vasodilation and vasoconstriction. The apelin receptor and the angiotensin II receptor have significant homology to each other, and from a viewpoint of vascular pathological physiology, apelin signaling is thought to play a potential role. From a view point of vascular function, the function of apelin signaling is expressed by the activity of the apelin receptor in endothelial cells, and apelin signaling functions to assist in vasculogenesis and vascular plasticity and induce low blood pressure in resting endothelial cells. In 2008, Eyies reported study results indicating that the expression of apelin under hypoxic conditions regulates the division of endothelial cells and vasculogenic regeneration. This is induced by the upregulation of the apelin gene under hypoxic conditions or is involved in the mitogenic activity of apelin in endothelial cells. On the other hand, apelin activates Akt to lower blood pressure. It regulates blood pressure in blood vessels, promotes angiogenesis, increases the production of NO, and prevents signaling from being caused by angiotensin II that causes arteriosclerosis and aortic aneurysm, thereby inhibiting the activity of angiotensin II. The function of apelin signaling in blood vessels and endothelial cells was demonstrated by a phenotype resulting from the invalidation of the ligand and the receptor gene. The results of an experiment performed on mice deficient in the apelin receptor indicated that vasoconstrictor angiotensin II increased, whereas "retinal vasculogenesis in mice deficient in apelin decreased. In addition, the apelin receptor has effects on other organs. Specifically, in the heart, the apelin receptor is expressed in the initial stage of embryogenesis and is involved in the regulation of blood pressure and blood flow. In the brain, the apelin receptor is expressed in the neurons of a region playing a role in water and diet intake and is involved in the regulation of hormones and body fluids. In addition, the apelin receptor is also expressed in the enterochromaffine cells of the digestive system, and is involved in the inhibition of histamine secretion, the inhibition of gastric acid secretion, the inhibition of insulin secretion that increased by glucose, or the regulation of blood glucose levels. Moreover, it is expressed in the surface of osteoblasts and is involved in bone formation. Thus, it is thought that apelin signaling by the apelin/APJ system will have a high therapeutic effect in patients having vascular disorders such as ischemic diseases or cardiovascular diseases, which are caused by impairment of regulation of this signaling, and other diseases (Dr Yves AUDIGIER. Institute of Molecular Medicine of Rangueil. Archived topic page last updated on 22 Sep. 2008. http://www.scitopics.com/APµELIN_SIGNALLING.html).

However, the function or activity of apelin is not known regarding the proliferation of stem cells. In an example of the present invention, it could be seen that, when mesenchymal stem cells were cultured in a medium containing apelin, the activity of the stem cells was maintained without changing the characteristics (such as morphology) of the cells, and the proliferation ability efficiently increased.

As apelin that is used in the present invention, commercially available apelin may be used, but is not limited thereto, and apelin prepared by synthesis may also be used. In an example of the present invention, a medium composition was used, which contains apelin at a concentration of 1-100 Nm, and preferably 20-50 nM. As apelin, catalog no H-4566 (powder form) purchased from Bachem was used after dissolution in a solvent (e.g., DMSO (dimethyl sulfoxide)).

When stem cells are cultured in the apelin-containing medium composition of the present invention, the ability of the stem cells to self-renew is improved without changing the morphology or activity of the stem cells. Thus, the use of the medium composition of the present invention makes it possible to obtain a large amount of stem cells without changing the characteristics of the cells (see Example 2).

The medium composition of the present invention may further comprise, in addition to apelin, one or more antioxidants selected from among selenium, ascorbic acid, vitamin E, catechin, lycopene, beta-carotene, coenzyme Q-10 (CoQ-10), resveratrol, T-BHQ, oltipraz, an *Alnus japonica* extract, eicosapentaenoic acid (EPA), and docosahexanoic acid (DHA). It could be seen that stem cells cultured in a medium composition containing apelin and the antioxidant also had an excellent ability to proliferate, without changing their morphology or activity. Herein, the antioxidant may be contained in an amount ranging from 1 µM to 20 µM based on 20 nM of apelin. In an example of the present invention, it could be seen that stem cells cultured in a medium containing apelin and coenzyme Q-10 had an excellent ability to proliferate (see Example 2).

Meanwhile, the medium composition of the present invention may comprise a basal medium which contains either apelin or a combination of apelin and one or more antioxidants selected from among selenium, ascorbic acid, vitamin E, catechin, lycopene, beta-carotene, coenzyme Q-10 (CoQ-10), resveratrol, T-BHQ, oltipraz, an *Alnus japonica* extract, EPA (eicosapentaenoic acid) and DHA (docosahexanoic acid), and which has a simple composition known in the art to be suitable for the culture of stem cells. The basal medium used in the present invention refers to a typical medium having a simple composition known as being suitable for the culture of stem cells in the art. Examples of the basal medium generally used to culture the stem cells include MEM (Minimal Essential Medium), DMEM (Dulbecco modified Eagle Medium), RPMI (Roswell Park Memorial Institute Medium), and K-SFM (Keratinocyte Serum Free Medium). As the basal medium used in the present invention, any mediums can be used without any limitation as long as they are used in the art. Preferably, the basal medium may be selected from the group consisting of M199/F12 (mixture) (GIBCO), MEM-alpha medium (GIBCO), low-concentration glucose-containing DMEM medium (Welgene), MCDB 131 medium (Welgene), IMEM medium (GIBCO), K-SFM, DMEM/F12 medium, PCM medium, and MSC expansion medium (Chemicon). Particularly, among them, K-SFM may be preferably used.

A basal medium that is used to obtain the cultured mesenchymal stem cells may be supplemented with additives known in the art, which promote the proliferation of mesenchymal stem cells in an undifferentiated state while inhibiting the differentiation thereof. Also, the medium may contain a neutral buffer (such as phosphate and/or high-concentration bicarbonate) in isotonic solution, and a protein nutrient (e.g., serum such as FBS, FCS (fetal calf serum) or horse serum, serum replacement, albumin, or essential or non-essential amino acid such as glutamine or L-glutamine). Furthermore, it may contain lipids (fatty acids, cholesterol, an HDL or LDL extract of serum) and other ingredients found in most stock media of this kind (such as insulin or transferrin, nucleosides or nucleotides, pyruvate, a sugar source such as glucose, selenium in any ionized form or salt, a glucocorticoid such as hydrocortisone and/or a reducing agent such as β-mercaptoethanol).

Also, for the purpose of preventing cells from adhering to each other, adhering to a vessel wall, or forming too large clusters, the medium may advantageously contain an anti-clumping agent, such as one sold by Invitrogen (Cat #0010057AE).

Among them, one or more of the following additional additives may advantageously be used:

stem cell factor (SCF, Steel factor), other ligands or antibodies that dimerize c-kit, and other activators of the same signaling pathway ligands for other tyrosine kinase related receptors, such as the receptor for platelet-derived growth factor (PDGF), macrophage colony-stimulating factor, Flt-3 ligand and vascular endothelial growth factor (VEGF)

factors that elevate cyclic AMP levels, such as forskolin factors that induce gp130 such as LIF or Oncostatin-M hematopoietic growth factors such as thrombopoietin (TPO)

transforming growth factors such as TGFβ1 neurotrophins such as CNTF antibiotics such as gentamicin, penicillin or streptomycin.

The medium composition of the present invention may contain, in addition to the basal medium, at least one component selected from the group consisting of N-acetyl-L-cysteine (NAC), insulin or insulin-like factor, hydrocortisone, dexamethasone, basic fibroblast growth factor (bFGF), heparan sulfate, 2-mercaptoethanol, and epidermal growth factor (EGF).

Specifically, the medium may contain insulin-like factor as insulin replacement, which functions to promote cell growth by enhancing glucose metabolism and protein metabolism. Particularly, recombinant IGF-1 (insulin-like growth factor-1) is preferably used. The preferred content of insulin-like factor is 10-50 ng/ml. If the content of insulin-like factor is less than 10 ng/ml, apoptosis will occur, and if the content is more than 50 ng/ml, it will increase the cytotoxicity and cost of the medium.

The medium may contain basic fibroblast growth factor (bFGF) that can induce various types of cell proliferation in vivo. Preferably, recombinant bFGF protein is used. The preferred content of bFGF is 1-100 ng/ml.

The medium that is used in the present invention may additionally contain a component selected from the group consisting of FBS (fetal bovine serum), calcium and EGF. Epidermal growth factor (EGF) preferably uses recombinant EGF protein. The preferred content of epidermal growth factor is 10-50 ng/ml. If the content of epidermal growth factor in the medium is less than 10 ng/ml, it will have no particular effect, and if the content is more than 50 ng/ml, it will be toxic to cells.

As stem cells used in the present invention, adult stem cells derived from adipose tissue of the adult stem cells or epithelial tissue such as a hair follicle or an amnion may be used. Preferably, mesenchymal stem cells (MSCs) are used. Most preferably, human adipose tissue-derived mesenchymal stem cells (AdMSCs) may be used.

Said adipose tissue or epithelial tissue is preferably derived from a mammal, more preferably a human. In one examples of the present invention, human adipose tissue-derived mesenchymal stem cells (AdMSCs) were used.

When stem cells are cultured in the medium composition of the present invention, it is possible to obtain stem cells having an improved ability to proliferate, without changing the characteristics of the stem cells.

In another aspect, the present invention is directed to a method for enhancing the self-renewal ability of stem cells, the method comprising a step of culturing stem cells in a medium composition containing apelin.

In an example of the present invention, adipose-derived mesenchymal stem cells were cultured in the medium of the present invention. Adipose-derived mesenchymal stem cells can be obtained in the following manner. First, human adipose tissue obtained from the abdomen by liposuction or the like is isolated and washed with PBS, after which the tissue is cut finely and degraded using DMEM medium containing collagenase. The degraded tissue is washed with PBS and centrifuged at 1000 rpm for 5 minutes. The supernatant is removed, and the pellet remaining at the bottom is washed with PBS, and then centrifuged at 1000 rpm for 5 minutes. The resulting cells are filtered through a 100-mesh filter to remove the debris, and then washed with PBS. The cells are cultured overnight in DMEM medium (10% FBS, 2 mM NAC, 0.2 mM ascorbic acid), and then the cells that did not adhere to the bottom of the culture container were washed out with PBS, and the cells are subcultured while the medium was replaced with K-SFM medium containing NAC, ascorbic acid, calcium, rEGF, insulin and hydrocortisone at 2-day intervals, thereby obtaining adipose-derived mesenchymal stem cells. In addition to this method, any method known in the art may also be used to obtain mesenchymal stem cells.

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1: Isolation of Human Adipose Tissue-Derived Mesenchymal Stem Cells

Adipose tissue was isolated from the abdominal subcutaneous tissue of each of persons in their 40s (n=1), 50s (n=1) and 60s (n=1) by liposuction, and then washed with PBS. The washed adipose tissue was cut finely, and then treated with a DMEM medium containing collagenase type 1 (1 mg/ml) at 37° C. for 2 hours. The collagenase-treated tissue was washed with PBS, and then centrifuged at 1000 rpm for 5 minutes. The supernatant was removed, and the pellets were washed with PBS and centrifuged at 1000 rpm for 5 minutes. The resulting cells were filtered through a 100 µm mesh filter to remove floating material, and then washed with PBS, after which the cells were cultured in a DMEM medium containing 10% FBS, 2 mM NAC (N-acetyl-L-cysteine) and 0.2 mM ascorbic acid.

After overnight, the non-adherent cells were washed out with PBS, and the cells were subcultured to passage 3 in a K-SFM medium containing 5% FBS, 2 mM NAC, 0.2 mM ascorbic acid, 0.09 mM calcium, 5 ng/ml rEGF, 5 µg/ml insulin, 10 ng bFGF, 74 ng/ml hydrocortisone and 1 ng/ml while the medium was replaced at 2-day intervals, thereby obtaining adipose mesenchymal stem cells.

Example 2: Identification of Medium Component Having Effect on Self-Renewal Ability of Stem Cells The adipose mesenchymal stem cells of three persons, obtained by subculture to passage 3 in Example 1, were seeded into each of the following media and cultured for 4 days. During 4 days of culture, the morphology of the cells was observed. In addition, the size, viability and CDPL (cell population doubling level) of the cells were measured and expressed as mean values.

Medium 1: dRK medium dRK medium is "K-SFM (keratinocyte-SFM) medium+2 mM NAC+0.2 mM ascorbic acid+0.09 mM calcium+5 µg/ml insulin+74 ng/ml hydrocortisone+antioxidant (selenium)".

Medium 2: M9 medium (control)

M9 medium is a medium obtained by excluding an antioxidant (selenium) from dRK medium.

Medium 3: M9 medium+0.07% DMSO (control)

Medium 4: dRK medium+3 factors 3 factors are 20 nM apelin+5 µM CoQ10+20 µM T-BHQ Medium 5: M9 medium+3 factors Medium 6: M9 medium+20 nM apelin Medium 7: M9 medium+50 nM apelin Medium 8: M9 medium+20 nM apelin+5 µM CoQ10

Medium 9: M9 medium+20 nM apelin+20 µM T-BHQ

Medium 10: M9 medium+20 nM apelin+1 µM Resveratrol

Medium 11: M9 medium+20 nM apelin+5 µg/ml *Alnus japonica* extract

Medium 12: M9 medium+20 nM apelin+10 µM oltipraz.

While the adipose mesenchymal stem cells isolated in Example 1 was cultured in each of the media, the adipose mesenchymal stem cells were collected at different days of culture, and the viability, cell size and CPDL of the cells were measured. Also, telomerase activity was measured for the cells subcultured to passage 3. The *Alnus japonica* extract in medium 11 was prepared in the following manner.

The bark of *Alnus japonica* (produced in China) was washed, settled in 80% alcohol, and extracted at 60° C. to obtain a first extract. The first extract was filtered, transferred into a concentration tank, and concentrated in vacuo at 60° C. to completely recover the alcohol. The first concentrate (solid content: 25%) was recovered, and the essential oil component attached to the inner wall of the tank was recovered by adding a small amount of alcohol to the tank and heating and dissolving it at 60° C. for 20-40 minutes. The recovered essential oil component was mixed with the first concentrate, thereby obtaining concentrate mixture (1). The first *Alnus japonica* bark extract was settled in the recovered 80% alcohol and further extracted at 60° C. for 10-16 hours to obtain a second extract. The second extract was filtered, and concentrated in vacuo in a concentration tank to completely recover the alcohol. The second concentrate (solid content: 25%) was recovered, and the essential oil component attached to the inner wall of the tank was recovered by adding a small amount of alcohol (95%) to the tank and heating and dissolving it at 60° C. The recovered essential oil component was mixed with the second concentrate, thereby obtaining concentrate mixture (2). Concentrate mixtures (1) and (2) (solid content: 25%) were mixed with each other, and an excipient (dextrin) was added thereto in an amount of 20% based on the solid content of the *Alnus japonica* bark extract, after which the mixture was spray-dried and packaged as fast as possible under a condition in which moisture would not penetrate the mixture.

(1) Morphology of Stem Cells

Figure 1:
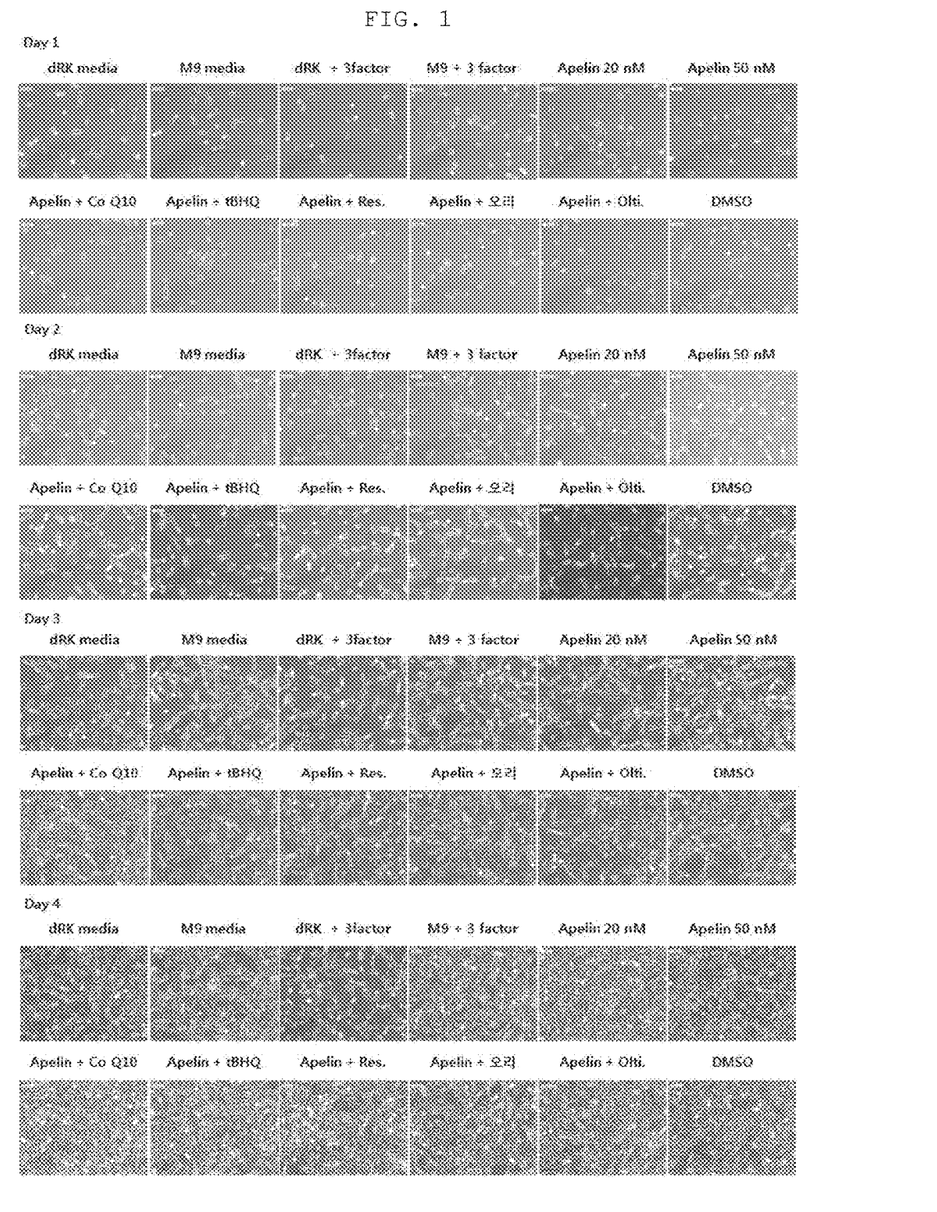
FIG. 1 shows microscopic photographs obtained by culturing adipose stem cells, isolated from people in their 40s, 50s and 60s, to passage 3 with media described in Example 1, and microscopically observing the morphology of the cells in each of the media up to day 4 after the culture of the cells.

The morphology of the stem cells was observed under a phase contrast microscope and photographed (see FIG. 1). The results of the observation indicated that there was no significant difference in the morphology. Thus, it could be seen that apelin or the antioxidant such as CoQ10 used in the present invention had no significant effect on the morphology of the cells.

(2) Viability of Stem Cells

TABLE 1

| Day (post seeding) | Media | | | | | | | | | | | |
|---|---|---|---|---|---|---|---|---|---|---|---|---|
| | dRK | M9 | DMSO | dRK + 3 factor | M9 + 3 factor | Apelin 20 nM | Apelin 50 nM | Ap + Co | Ap + tBHQ | Ap + Res | Ap + *Alnus japonica* | Ap + Olti |
| Day 1 | 95.2 | 97.2 | 96.4 | 93.3 | 96.4 | 97.2 | 91.7 | 96.4 | 92.5 | 95.9 | 91.7 | 94.1 |
| Day 2 | 97.4 | 95 | 98.8 | 96.3 | 98.4 | 98.9 | 100 | 99.2 | 98.2 | 99 | 97.8 | 99 |
| Day 3 | 97.1 | 99 | 98.1 | 98.8 | 97.7 | 98.8 | 98.8 | 99.4 | 99.1 | 99.5 | 99.4 | 99.2 |
| Day 4 | 99.1 | 98.8 | 99.1 | 98.1 | 99.2 | 99.4 | 99.2 | 99.2 | 99 | 98.6 | 99.2 | 98.9 |

Figure 2:
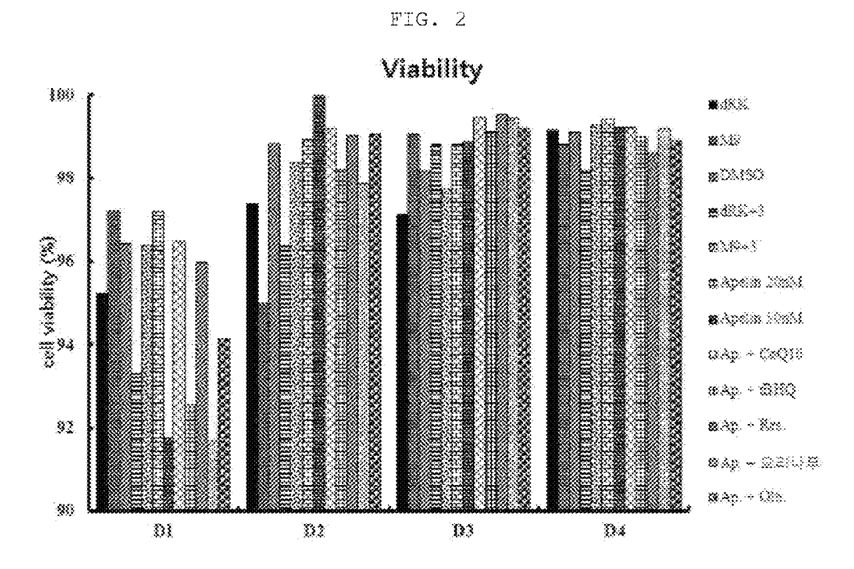
FIG. 2 is a graph showing the viability of adipose stem cells, obtained by culturing adipose stem cells, isolated from people in their 40s, 50s and 60s, to passage 3 with media described in Example 1, and measuring the viability of the cells in each of the media up to day 4 after the culture of the cells.

The results of the experiment indicated that there was no significant difference in the viability of the stem cells between the components added. Thus, it could be seen that apelin or the antioxidant such as CoQ10 used in the present invention had no significant effect on the viability of the cells (see FIG. 2). The viability of the stem cells was measured using Luna™ automated cell counter (n=3).

(3) Size of Stem Cells

TABLE 2

| Day (post seeding) | Media | | | | | | | | | | | |
|---|---|---|---|---|---|---|---|---|---|---|---|---|
| | dRK | M9 | DMSO | dRK + 3 factor | M9 + 3 factor | Apelin 20 nM | Apelin 50 nM | Ap + Co | Ap + tBHQ | Ap + Res | Ap + *Alnus japonica* | Ap + Olti |
| Day 1 | 19.4 | 18.8 | 18.8 | 19.9 | 18.4 | 19.0 | 18.6 | 18.9 | 18.3 | 18.7 | 18.3 | 19.4 |
| Day 2 | 18.8 | 14.9 | 16.8 | 19.2 | 17.3 | 18.3 | 15.6 | 17.9 | 17.0 | 17.7 | 17.3 | 17.3 |
| Day 3 | 18.6 | 16.6 | 15.9 | 19.4 | 17.6 | 18.2 | 18.0 | 17.0 | 16.6 | 15.4 | 16.3 | 17.5 |
| Day 4 | 20.3 | 18.7 | 17.1 | 19.7 | 18.6 | 18.5 | 17.9 | 18.8 | 18.7 | 17.6 | 17.4 | 18.6 |

Figure 3:
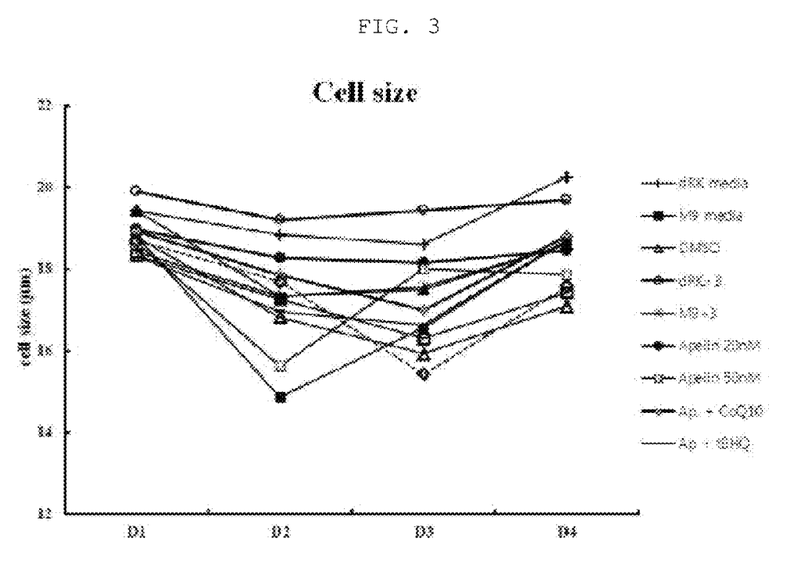
FIG. 3 is a graph showing the size of adipose stem cells, obtained by culturing adipose stem cells, isolated from people in their 40s, 50s and 60s, to passage 3 with media described in Example 1, and measuring the size of the cells in each of the media up to day 4 after the culture of the cells.

The adipose mesenchymal stem cells isolated in Example 1 were seeded in each of the media, and then treated with trypsin at different days of culture. Next, the adipose mesenchymal stem cells were collected, and the size (μm) of the stem cells was measured using Luna™ automated cell counter (n=3). The results of the measurement indicated that there was no significant difference in the cell size between the components added (see FIG. 3). Thus, it could be seen that apelin or the antioxidant such as CoQ10 used in the present invention had no significant effect on the size of the cells.

(4) Cell Population Doubling Level (CPDL) of Stem Cells

TABLE 3

| Day (post seeding) | Media | | | | | | | | | | | |
|---|---|---|---|---|---|---|---|---|---|---|---|---|
| | dRK | M9 | DMSO | dRK + 3 factor | M9 + 3 factor | Apelin 20 nM | Apelin 50 nM | Ap + Co | Ap + tBHQ | Ap + Res | Ap + *Alnus japonica* | Ap + Olti |
| Day 0 | 0.00 | 0.00 | 0.00 | 0.00 | 0.00 | 0.00 | 0.00 | 0.00 | 0.00 | 0.00 | 0.00 | 0.00 |
| Day 1 | 0.29 | 0.23 | 0.07 | 0.41 | 0.10 | 0.89 | 0.56 | 0.46 | 0.66 | 0.23 | −0.19 | 0.51 |
| Day 2 | 1.67 | 0.43 | 1.38 | 1.78 | 1.60 | 2.84 | 1.65 | 2.45 | 1.92 | 2.03 | 0.86 | 2.19 |
| Day 3 | 4.46 | 3.51 | 4.46 | 4.65 | 5.06 | 6.54 | 5.11 | 6.07 | 4.76 | 4.59 | 3.80 | 5.53 |
| Day 4 | 6.83 | 6.05 | 7.22 | 7.09 | 8.18 | 9.28 | 8.20 | 9.64 | 8.11 | 7.59 | 6.80 | 8.43 |

The cell population doubling level (CPDL) of the stem cells was calculated using the following equation:

$$CPDL = \text{Log}(N_{final} - N_{initial})/\text{Log } 2,$$

wherein $N_{final}$: the number of finally obtained cells; and $N_{initial}$: the number of initially seeded cells.

Figure 4:
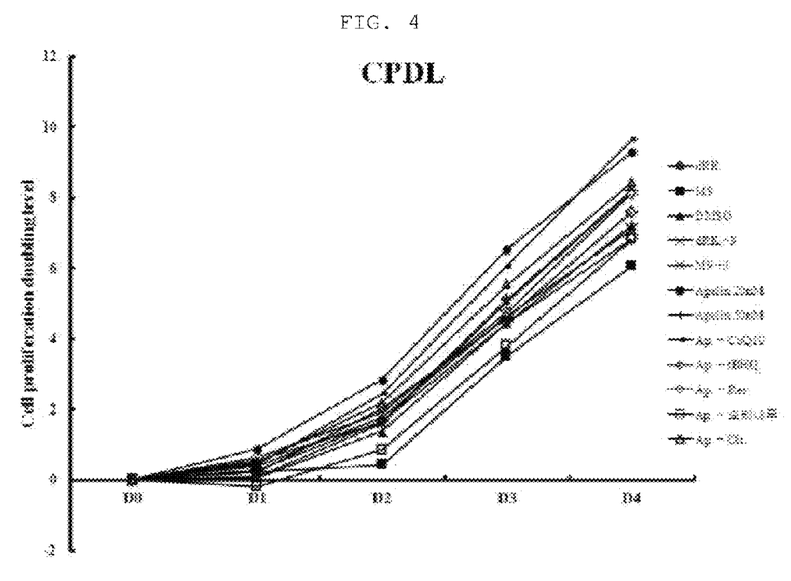
FIG. 4 is a graph showing the CPDL (cell population doubling level) of adipose stem cells, obtained by culturing adipose stem cells, isolated from people in their 40s, 50s and 60s, to passage 3 with media described in Example 1, and measuring the CPDL of the cells in each of the media up to day 4 after the culture of the cells.

The results of the experiment indicated that, when stem cells were cultured in the media containing apelin or when stem cells were cultured in the media containing apelin together with antioxidants, the CPDL of the cells increased, suggesting that the self-renewal ability of the cells was improved (see FIG. 4). Among the media containing apelin together with antioxidants, the medium containing apelin together with CoQ10 or oltipraz showed the highest CPDL. In addition, the medium comprising dRK medium+3 factors (3 factors=apelin+coQ10+T-BHQ) showed a higher CPDL compared to dRK medium or M9 medium alone, but showed a lower CPDL compared to other two mixed media. Thus, it could be seen that the antioxidant contained in dRK medium reduced the effects of the 3 factors.

(5) Measurement of Telomerase Activity of Stem Cells

TABLE 4

| Media | telomerase activity (N = 3) |
|---|---|
| dRK | 2.593 |
| M9 | 2.249 |
| M9 + Oltipraz (7 μM) | 1.968 |

TABLE 4-continued

| Media | telomerase activity (N = 3) |
|---|---|
| M9 + Oltipraz (10 μM) | 2.137 |
| M9 + Resveratrol (1 μM) | 2.042 |
| M9 + Resveratrol (2 μM) | 1.654 |

TABLE 4-continued

| Media | telomerase activity (N = 3) |
|---|---|
| M9 + TBH-Q (5 μM) | 2.524 |
| M9 + TBH-Q (20 μM) | 2.838 |
| M9 + Coenzyme Q10 (5 μM) | 2.817 |
| M9 + Coenzyme Q10 (10 μM) | 1.964 |
| M9 + Apelin (5 nM) | 2.838 |
| M9 + Apelin (20 nM) | 3.068 |
| M9 + *Alnus japonica* extract (5 μg/ml) | 2.415 |
| M9 + *Alnus japonica* extract (10 μg/ml) | 1.885 |

Adipose mesenchymal stem cells isolated from persons in their 40s, 50s and 60s according to the method of Example 1 were cultured to passage 3 in each of the media shown in Table 4 above, and then the telomerase activity of the stem cells was measured using Telo TAGGG Telomerase PCR ELISA kit (Roche). The results of the measurement indicated that the stem cells cultured in the medium containing apelin at concentration of 20 nM showed the highest telomerase activity.

INDUSTRIAL APPLICABILITY

As described above, according to the present invention, the self-renewal ability of stem cells can be enhanced without changing the characteristics (such as activity or size) of the cells even when the cells are repeatedly cultured. Accordingly, a large amount of stem cells can be obtained within a short period of time, and thus the efficacy of cell therapy based on stem cells can be significantly improved.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for preparing stem cells having enhanced proliferative character and telomerase activity, wherein the method comprises:
   providing isolated mesenchymal stem cells for culturing;
   seeding the provided mesenchymal stem cells into a basal medium composition; and
   culturing the mesenchymal stem cells in the basal medium composition, wherein the basal medium composition contains apelin at a concentration of 20-100 nM and wherein antioxidant when present in said basal medium composition has a ratio of micromolar concentration of antioxidant, to nanomolar concentration of apelin, that is in a ratio of 0.05 to 1, to yield cultured mesenchymal stem cells having a cell population doubling level (CPDL) and telomerase activity that are enhanced in relation to cell population doubling level (CPDL) and telomerase activity of the provided mesenchymal stem cells when correspondingly cultured in a basal medium composition lacking apelin therein.

2. The method of claim 1, wherein the mesenchymal stem cells are adipose tissue-derived stem cells.

3. The method of claim 1, wherein the medium composition further comprises one or more selected from the group consisting of selenium, ascorbic acid, vitamin E, catechin, lycopene, beta-carotene, coenzyme Q-10 (CoQ-10), resveratrol, T-BHQ, oltipraz, an *Alnus japonica* extract, eicosapentaenoic acid (EPA), and docosahexanoic acid (DHA).

4. The method of claim 1, wherein the medium composition further comprises coenzyme Q-10 (CoQ-10) or oltipraz.

5. The method of claim 1, wherein the medium composition comprises at least one component selected from the group consisting of N-acetyl-L-cysteine (NAC), insulin or insulin-like factor, hydrocortisone, dexamethasone, basic fibroblast growth factor (bFGF), heparan sulfate, 2-mercaptoethanol, and epidermal growth factor (EGF).

* * * * *

UNITED STATES PATENT AND TRADEMARK OFFICE
CERTIFICATE OF CORRECTION

PATENT NO.         : 9,982,234 B2
APPLICATION NO.    : 14/889434
DATED              : May 29, 2018
INVENTOR(S)        : Jeong-Chan Ra et al.

It is certified that error appears in the above-identified patent and that said Letters Patent is hereby corrected as shown below:

In the Specification

In Column 1, at Line 5, below the title "CULTURE MEDIUM COMPOSITION FOR IMPROVING REGENERATIVE CAPACITY OF STEM CELLS, AND STEM CELL CULTURING METHOD USING SAME" and before the heading "TECHNICAL FIELD", the following should be inserted:
-- CROSS-REFERENCE TO RELATED APPLICATIONS
This application is a U.S. national phase under the provisions of 35 U.S.C. § 371 of International Patent Application No. PCT/KR14/01013 filed February 6, 2014, which in turn claims priority of Korean Patent Application No. 10-2013-0052558 filed May 9, 2013. The disclosures of such international patent application and Korean priority patent application are hereby incorporated herein by reference in their respective entireties, for all purposes. --

Signed and Sealed this
Twenty-fourth Day of July, 2018

Andrei Iancu
*Director of the United States Patent and Trademark Office*